United States Patent
Johs et al.

(10) Patent No.: US 7,295,313 B1
(45) Date of Patent: *Nov. 13, 2007

(54) APPLICATION OF INTERMEDIATE WAVELENGTH BAND SPECTROSCOPIC ELLIPSOMETRY TO IN-SITU REAL TIME FABRICATION OF MULTIPLE LAYER ALTERNATING HIGH/LOW REFRACTIVE INDEX FILTERS

(75) Inventors: Blaine D. Johs, Lincoln, NE (US);
Jeffrey S. Hale, Lincoln, NE (US);
John A. Woollam, Lincoln, NE (US);
Craig M. Herzinger, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 526 days.

This patent is subject to a terminal disclaimer.

(21) Appl. No.: 10/943,821

(22) Filed: Sep. 17, 2004

Related U.S. Application Data

(63) Continuation-in-part of application No. 10/194,881, filed on Jul. 15, 2002, now Pat. No. 6,940,595, and a continuation-in-part of application No. 09/916,836, filed on Jul. 27, 2001, now Pat. No. 6,636,309, said application No. 10/194,881.

(60) Provisional application No. 60/305,535, filed on Jul. 14, 2001.

(51) Int. Cl.
*G01J 4/00* (2006.01)

(52) U.S. Cl. .................................................. 356/369
(58) Field of Classification Search ................. 356/369
See application file for complete search history.

(56) References Cited

U.S. PATENT DOCUMENTS

| | | | |
|---|---|---|---|
| 6,297,880 B1 * | 10/2001 | Rosencwaig et al. ....... | 356/369 |
| 6,636,309 B1 | 10/2003 | Johs et al. .................. | 356/369 |
| 6,781,692 B1 | 8/2004 | Rosencwaig ................ | 356/369 |
| 6,940,595 B1 * | 9/2005 | Johs et al. .................. | 356/369 |
| 2002/0113966 A1 * | 8/2002 | Shchegrov et al. ......... | 356/369 |
| 2003/0053053 A1 * | 3/2003 | Opsal et al. ................ | 356/369 |
| 2004/0207844 A1 * | 10/2004 | Nabatova-Gabain et al. .... | 356/369 |

* cited by examiner

*Primary Examiner*—Tarifur Chowdhury
*Assistant Examiner*—Isiaka O Akanbi
(74) *Attorney, Agent, or Firm*—James D. Welch

(57) ABSTRACT

Disclosed is application of oblique angle of incidence, reflection and/or transmission mode spectroscopic ellipsometry PSI and/or DELTA, (including combinations thereof and/or mathematical equivalents), vs. wavelength data over an intermediate wavelength band range around a pass or reject band, to monitor and/or control fabrication of multiple layer high/low refractive index band-pass, band-reject and varied attenuation vs. wavelength thin film interference filters, either alone or in combination with transmissive non-ellipsometric electromagnetic beam turning point vs. layer data obtained at an essentially normal angle of incidence.

17 Claims, 7 Drawing Sheets

APPLICATION OF INTERMEDIATE WAVELENGTH BAND SPECTROSCOPIC ELLIPSOMETRY TO IN-SITU REAL TIME FABRICATION OF MULTIPLE LAYER ALTERNATING HIGH/LOW REFRACTIVE INDEX FILTERS

This Application is a CIP of Allowed applications Ser. No. 10/194,881, Filed Jul. 15, 2002 now U.S. Pat. No. 6,940,595; and of Ser. No. 09/916,836 filed Jul. 27, 2001 now U.S. Pat. No. 6,636,309 and therevia Claims benefit of Provisional Application Ser. No. 60/305,535 Filed Jul. 14, 2001.

TECHNICAL FIELD

The disclosed invention relates to application of Intermediate Wavelength Band Ellipsometry to in-situ real-time monitoring and/or process control; and more precisely to the monitoring and/or controlling of the fabrication of multiple layer high/low refractive index Band-Pass, Band-Reject or Varied Attenuation vs. Wavelength filters comprising use of oblique angle-of-incidence Spectroscopic Ellipsometric Parameter vs. Wavelength data determined over wavelength range(s) in which reflectivity and/or transmisivity is relatively constant. Said method is optionally enhanced by combination with, or compliments use of conventional non-ellipsometric transmission intensity extrema turning point vs. layer data, obtained at a substantially normal angle-of-incidence.

BACKGROUND

The use of Spectroscopic Ellipsometry (SE) to non-invasively characterize properties, (such as thickness, composition, morphology and optical constants), of thin films ex-situ is well known. And, while less common, application to real-time in-situ fabrication monitoring and control is also known, particularly in the semiconductor area. Further, it is known that said techniques are directly applicable to investigating sample systems comprised of multiple thin film layers.

Ellipsometry basically monitors a change in Polarization State of a beam of electromagnetism, which polarization state change occurs as a result of interaction with a sample system. Based upon said change in polarization state, sample system characterizing ellipsometric PSI ($\Psi$) and ellipsometric DELTA ($\Delta$), which are defined by:

$$\rho = rp/rs = \text{Tan}(\Psi)\exp(i\Delta)$$

where $r_p$ and $r_s$ can be complex Fresnel reflectivities for "p" and "s" polarized components, can be determined. It is noted that Rho ($\rho$) is a complex number defined as the ratio of the reflectivity of "p-polarized" to reflectivity of the "s-polarized" components of a beam of polarized electromagnetic radiation. In polar form, Tan($\Psi$) corresponds to the magnitude of the reflectivity ratio and ($\Delta$) corresponds to the phase angle introduced between "p" and "s" polarized components by interaction with the sample system. Further, it should be understood that said "p" component is defined as being in the plane of an incident and reflected beam of electromagnetic radiation, which plane also contains a normal to the surface of the reflective surface of the sample system. And the "s" component is defined as being perpendicular to the direction of the "p" component and also parallel to said reflective surface of the sample system.

It should be appreciated that ellipsometry determines a ratio of "p" and "s" polarization component intensity values rather than an absolute intensity value, and that ellipsometry provides phase shift information, (ie. between said "p" and "s" components), which is not available from electromagnetic beam intensity reflection or transmission data, wherein change in "p" and "s" polarization states are not monitored. It is further to be appreciated that said phase shift information is generally very sensitive to properties, (and changes therein), associated with ultra-thin films.

It should also be appreciated that many types of Ellipsometer systems exist which sequentially comprise a source of electromagnetic radiation, a polarizer means for setting a polarization state, a means for supporting a sample system, an analyzer means for selecting a polarization state, and a detector means for receiving electromagnetic radiation and producing a signal which is proportional to its intensity. Typically at least one element in the ellipsometer system is caused to rotate during data acquisition, and said rotating element can be the polarizer means or analyzer means. A problem in applying rotating polarizer or rotating analyzer ellipsometer systems, however, is that ellipsometric DELTA's of 0.0 or 180 degrees are very difficult to measure therewith out use of means such as the J.A. Woollam Co. Autoretarder, (see U.S. Pat. Nos. 5,757,494 and 5,956,145). In that light it is disclosed that a relevant benefit exists where the polarizer means and analyzer means are both held essentially stationary during data acquisition, and instead an additional element, (ie. a compensator), is present and rotated during said data acquisition. The reason for this is that rotating compensator ellipsometers can measure ellipsometric DELTA's over the entire range of 0.0-360 degrees. In addition, rotating compensator ellipsometer systems can measure ellipsometric PSI's over the entire range of 0.0 to 90 degrees. The J.A. Woollam Co. "M2000" (Reg. Trademark), Rotating Compensator Ellipsometer System is described in U.S. Pat. No. 5,872,630 which is incorporated by reference hereinto.

Continuing, of growing importance is the fabrication and application of multiple High/Low Refractive Index Band-Pass and Band-Reject Filters. For instance, Band-Pass Filters which provide very sharp passband cutoff characteristics, (eg. passbands providing a bandwidth of a nanometer or so with combined high and low side transition to cutoff being less than a nm), are typically comprised of up to a hundred or more layers of alternating quarter-wavelength optical thickness high, and quarter wavelength low optical thickness, refractive index materials, said sequence being beneficially interspersed with half-wavelength thick cavities and/or coupling layers. (Note, "optical thickness" is defined as the index of refraction times the physical thickness). Present manufacturing techniques typically control deposition of the layers of alternating quarter-wavelength high, and quarter wavelength low, optically thick refractive index materials utilizing optical transmission data, wherein a cyclic pattern of Intensity Transmission vs.

Layer Number "extrema" turning points are used to determine when to change from depositing low to high, and vice-verse, refractive index material. A problem with this approach is that in some physical thickness and/or wavelength ranges said Intensity Transmission "extrema" turning point data can be relatively insensitive to change in thickness of deposited material, particularly where other than quarter-wavelength optical thickness layers are deposited.

A Search of Patents which apply ellipsometry in the fabrication of multiple layer stack systems, (such as multiple High/Low Refractive Index Layers), has identified very little. The following Patents are disclosed, however, as they mention Ellipsometry in a relevant context:

U.S. Pat. No. 6,781,692 to Rosencwaig describes the use of Narrow Band and Broad Band Wavelength Ranges in a method of manufacturing multilayer, thin film interference filters, comprising the steps of:

depositing a plurality of thin film layers on a substrate, the plurality of thin film layers forming a multilayer, thin film interference filter;

monitoring the formation of at least some of the thin film layers during the deposition process, said monitoring step including the steps of:

directing a narrow, (or broad) band radiation probe to reflect off the layers on the substrate;

monitoring the change in polarization state of the probe beam induced by the interaction with the layers and generating output signals in response thereto; and controlling the deposition process based on the monitored signal.

It is specifically noted that use of an Intermediate Wavelength Band is not described in the 692 patent, and it is disclosed at this point that the present invention Claims use of an Intermediate Wavelength band in fabrication of thin film interference filters, where the terminology "Intermediate band" is given specific definition, (see the Disclosure of the Invention and Detailed Description Sections herein). Note, the 692 patent, in Col. 3, Lines 40-67 indicates what is meant by Narrow and Broad Band therein.

U.S. Pat. No. 6,051,113 to Moslehi, which discusses apparatus and methodology for multi-target physical vapor deposition of multi-layer materials structures;

U.S. Pat. No. 4,793,908 to Scott et al., which discusses multiple ion source method and apparatus for fabricating multilayer optical films;

U.S. Pat. No. 4,934,788 to Southwell, which discusses deposition of gradient index coatings using coevaporation with rate control; and U.S. Pat. No. 6,104,530 to Okamura et al., which discusses transparent laminates and optical filters for displays.

U.S. Pat. No. 5,091,320 to Aspnes et al. which discusses ellipsometric control of material growth.

U.S. Pat. No. 4,770,895 to Hartley which discusses ellipsometric control of material growth.

Articles which discuss application of ellipsometry to real time applications are:

A paper titled "Extension of Multichannel Spectroscopic Ellipsometry Into The Ultraviolet for Real-Time Characterization of the Growth of Wide Bandgap Materials from 1.5 to 6.5 ev", Zapien et al., Mat. Res. Soc. Symp., Proc. Vol. 569 (1999).

"Instrumental and Computational Advances for Real-time Process Control Using Spectroscopic Ellipsometry", Pickering et al., Int. Conf. on Metrology and Characterization for VLSI Technology, NIST Gaithersburg, (March 1998).

A Reflectance Anisotropy Spectrometer for Real-time Measurements", Acher et al., Rev. Sci. Instrum. 63 (11), (November 1992).

Also disclosed is an Article by the Inventors titled "Optical Metrology Roadmap for the Semiconductor, Optical, and Data Storage Industires II", Johs et al., SPIE Vol 4449, (2001), which is incorporated hereinto by reference.

Even in view of known prior art, there remains need for improved methodology for monitoring and/or controlling fabrication of multiple layer High/Low Refractive Index stacks such as comprise Band-Pass, Band-Reject and Varied Attenuation vs. Wavelength Filters.

DISCLOSURE OF THE INVENTION

The disclosed invention is based in the discovery that, over a limited range of wavelengths surrounding the central passband band of a multiple Layer High/Low Refractive Index Band-Pass Filter, ellipsometric DELTA vs. wavelength, which are determined using data obtained by oblique angle spectroscopic ellipsometric investigation, are very well behaved. Further, it has been found that the High and Low Refractive Index materials demonstrate easily differentiated ellipsometric DELTA vs. Wavelength plots, and that said ellipsometric DELTA vs. wavelength, obtained by use of oblique angle reflection ellipsometry are primarily related to optical thickness of the surface layer of a Band-Pass Filter investigated during fabrication, with only minimal influence on said DELTA's being effected by previously deposited layers.

Similar beneficial results are available where ellipsometric PSI and/or DELTA are investigated in transmission over a limited region around a reject band in a Band-Reject Filter.

Presently, where quarter-wavelength optical thickness layers are being formed, Transmission Intensity Extrema Turning Point vs. Layer Number data is the primary approach utilized during fabrication of multiple layer Filters to provide generally good insight as to when to change from deposition of high to low, and low to high refractive index materials. However, where other than quarter-wavelength optical thickness layers are being formed said transmission extrema turning point data is often not sufficient to provide reliable data upon which a decision can be based. It is in that light that the disclosed invention teaches supplementing said conventional Transmission Intensity Extrema Turning Point vs. Layer Number data, with ellipsometric DELTA vs. wavelength data, to improve fabrication precision.

It should be appreciated that the disclosed invention methodology can, however, be applied alone, (ie. not in supplemental combination with conventional Transmission Intensity Extrema Turning Point vs. Layer Number data). The disclosed invention teaches use of ellipsometric DELTA vs. wavelength data alone to monitor and/or control deposition of quarter-wavelength, and especially non-quarter wavelength thickness layers during fabrication of multilayer Band-Pass and ellipsometric PSI and DELTA vs. wavelength when Band-Reject Filters are being fabricated. In the case of Band Pass Filter fabrication this is especially true as said ellipsometric DELTA vs. wavelength data obtained from electromagnetic beams which interact at an oblique reflection angle with the top surface of a Filter being fabricated provides insight primarily to the optical thickness of a layer of material, be it a high or low refractive index material, being deposited, said layer of material being immediately at the surface regardless of the stage of fabrication. Where Band Reject Filters are fabricated, and oblique angle Transmission ellipsometry is practiced, the identified top layer effect is not so pronounced, however, beneficial results are still obtainable when appropriate wavelength range(s) are selected and used to determine the ellipsometric parameters.

A disclosed invention method of manufacturing a multilayer, thin film interference filters, comprises the steps of:

depositing a plurality of thin film layers on a substrate, the plurality of thin film layers forming a multilayer, thin film interference filter;

monitoring the formation of at least some of the thin film layers during the deposition process, said monitoring step including the steps of:

directing an intermediate band radiation probe to reflect off the layers on the substrate;

monitoring the change in polarization state of the probe beam induced by the interaction with the layers and generating output signals in response thereto; and controlling the deposition process based on the monitored signal.

It is noted that the thin film interference intermediate filter can be:

a band-pass filter, in which intermediate band of wavelengths is defined by a region around a central pass band in which the reflectivity properties are substantially uniform;

a band-reject filter, in which intermediate band of wavelengths is defined by a region around a central pass band in which the transmisivity properties are substantially uniform;

a varied attenuation filter, in which intermediate band of wavelengths is defined by a region around a central pass or rejection band in which the reflectivity or transmisivity properties, respectively, are substantially uniform.

A disclosed invention method of monitoring and/or controlling fabrication of multiple High/Low Refractive Index Layer Filters which transmit a central passband of wavelengths while rejecting wavelengths outside thereof, then comprises the steps of;

in either order practicing steps a and b:

a. providing a system for fabricating Band-Pass Filters which comprises means for depositing alternating layers of High and Low refractive Index materials onto a substrate; and b. providing a spectroscopic ellipsometer system;

c. applying said spectroscopic ellipsometer system to said system for fabricating Band-Pass Filters such that a substrate can be monitored in a reflective mode, by a beam of intermediate wavelength band polarized spectroscopic electromagnetic radiation provided by said spectroscopic ellipsometer system, said spectroscopic ellipsometer system being oriented so as to direct an intermediate wavelength band beam of polarized spectroscopic electromagnetic radiation upon said substrate surface at an oblique angle;

d. placing a substrate into said system for fabricating Band-Pass Filters;

e. while depositing a plurality of alternating High and Low Refractive Index layers onto said substrate, in real-time determining Ellipsometric DELTA vs. wavelength data;

f. utilizing the resulting Ellipsometric DELTA vs. wavelength data to monitor and/or control the fabrication process.

Said method can further comprise, in combination with step b, the steps of:

b'. providing an essentially monochromatic central passband wavelength source of electromagnetic radiation, and a detector thereof, and c'. orienting said essentially central passband monochromatic wavelength source of electromagnetic radiation and detector thereof such that a beam of electromagnetic radiation is provided by said essentially monochromatic central passband wavelength source of electromagnetic radiation substantially along a normal to the surface of the substrate, transmits through said substrate and enters said detector.

When said steps b'. and c'. are added the method then further comprises obtaining real-time electromagnetic radiation Transmission data, and utilizing the results thereof in combination with the spectroscopic ellipsometric data in practicing step f. This can involve, for instance, using the transmission data to determine a sequence of extrema turning points in a plot of transmission intensity vs. layer number, and using said extrema turning points to determine when to change from depositing high to low and low to high refractive index materials when depositing quarter-wavelength optical thickness layers. When this is done, the Ellipsometric DELTA data, which typically comprises a sequence of DELTA values vs. wavelength, is then used to determine when to change from depositing high to low and low to high refractive index materials when depositing other than quarter-wavelength optical thickness layers, and to supplement the transmission data where said data indicates low sensitivity to quarter-wave optical thickness layer fabrication results.

A preferred embodiment of the recited method of monitoring and/or controlling fabrication of Band-Pass Filters further comprises a step of determining an intermediate wavelength band wavelength range, around the central Band-Pass wavelengths, in which reflectivity of the Band-Pass Filter being fabricated is expected to be relatively constant, and during the step e. determination of Ellipsometric DELTA vs. wavelength, limiting determination of the ellipsometric DELTA vs. wavelength using only that intermediate wavelength band range of wavelengths. It has been found that the DELTA vs. wavelength data obtained without practice of this step is of marginal utility. Said preferred embodiment can also include excluding the central passband wavelengths during said ellipsometric DELTA vs. wavelength determination.

A more detailed recitation of the disclosed invention methodology for monitoring and/or controlling fabrication of multiple High/Low Refractive Index Layer Band-Pass Filters which transmit a central passband of wavelengths while rejecting wavelengths outside thereof, comprises the steps of;

in either order practice of steps a and b:

a. providing a system for fabricating Band-Pass Filters which comprises means for depositing alternating layers of High and Low refractive Index materials onto a substrate; and b. providing a spectroscopic ellipsometer system and an essentially monochromatic transmission system;

c. applying said spectroscopic ellipsometer system to said system for fabricating Band-Pass Filters such that a substrate can be monitored in a reflective mode, by a intermediate wavelength band beam of polarized spectroscopic electromagnetic radiation provided by said spectroscopic ellipsometer system, said spectroscopic ellipsometer system being oriented so as to direct an intermediate wavelength band beam of polarized spectroscopic electromagnetic radiation onto said substrate surface at an oblique angle;

c'. applying said essentially monochromatic transmission system to said system for fabricating Band-Pass Filters such that a substrate can be monitored in a transmissive mode by a beam of electromagnetic radiation which is provided by said essentially monochromatic central passband wavelength source of electromagnetic radiation, said essentially monochromatic transmission monitoring system being oriented to direct a beam of essentially monochromatic radiation substantially along a normal to the surface of the substrate;

d. placing a substrate into said system for fabricating Band-Pass Filters;

e. in conjunction with the other steps, determining an intermediate wavelength band range around a central band pass wavelength of the Band-Pass Filter in which reflectivity thereof to a beam of electromagnetic radiation impinged at an oblique angle to a surface thereof is expected to be relatively constant;

f. while depositing a plurality of alternating High and Low Refractive Index layers onto said substrate, determining both transmission data in the central passband wavelengths, and Ellipsometric DELTA vs. wavelength in the range of wavelengths identified in step e., said determined transmission data comprising a sequence of extrema turning points in a plot of transmission intensity vs. layer number, and said determined ellipsometric DELTA data comprising a sequence of DELTA values vs. wavelength;

g. utilizing the resulting Transmission intensity extrema turning point and Ellipsometric DELTA vs. wavelength data to monitor and/or control the fabrication process, said intensity extrema turning point data being primarily used to determine when to change from depositing high to low and low to high refractive index materials when depositing quarter-wavelength optical thickness layers, and said ellipsometric DELTA vs. wavelength data being primarily used to determine when to change from depositing high to low and low to high refractive index materials when depositing other than quarter-wavelength optical thickness layers, and otherwise supplementing the intensity extrema turning point data.

Again, said method of monitoring and controlling fabrication of Band-Pass Filters can include excluding the central passband wavelengths from the range of wavelengths over which the ellipsometric DELTA vs. wavelength is determined as identified in step e., and utilized in step f.

The disclosed invention is also applicable in monitoring and/or controlling fabrication of Band-Reject Filters.

A disclosed invention method of monitoring and/or controlling fabrication of multiple High/Low Refractive Index Layer Filters which reject a central band of wavelengths while passing wavelengths outside thereof, then comprises the steps of;

a. providing a system for fabricating Band-Reject Filters which comprises means for depositing alternating layers of High and Low refractive Index materials onto a substrate; and b. providing a spectroscopic ellipsometer system;

c. applying said spectroscopic ellipsometer system to said system for fabricating Band-Reject Filters such that a substrate can be monitored in a transmission mode, by an intermediate wavelength band beam of polarized spectroscopic electromagnetic radiation provided by said spectroscopic ellipsometer system, said spectroscopic ellipsometer system being oriented so as to direct an intermediate wavelength band beam of polarized spectroscopic electromagnetic radiation upon said substrate surface at an oblique angle;

d. placing a substrate into said system for fabricating Band Reject Filters;

e. while depositing a plurality of alternating High and Low Refractive Index layers onto said substrate, in real-time determining a selection from the group consisting of:

Ellipsometric DELTA vs. wavelength;

Ellipsometric PSI vs. wavelength; and both Ellipsometric PSI and DELTA vs. wavelength;

f. utilizing the resulting Ellipsometric data to monitor and/or control the fabrication process.

Said method can further comprise, in combination with step b, the steps of:

b'. providing a source of electromagnetic radiation which provides wavelengths which are not rejected, and a detector thereof, and c'. orienting said source of electromagnetic radiation and detector thereof such that a beam of electromagnetic radiation is provided and progresses along a normal to the surface of the substrate, transmits through said substrate and enters said detector.

When said steps b'. and c'. are added the method then further comprises obtaining real-time electromagnetic radiation non-ellipsometric Transmission data, and utilizes the results thereof in combination with the spectroscopic ellipsometric data in practicing step f. This can involve, for instance, using the electromagnetic radiation non-ellipsometric Transmission data transmission data to determine a sequence of extrema turning points in a plot of transmission intensity vs. layer number, and using said extrema turning points to determine when to change from depositing high to low and low to high refractive index materials when depositing quarter-wavelength optical thickness layers. The Ellipsometric data, which typically comprises a sequence of Ellipsometric Parameter(s) values vs. wavelength, is used to determine when to change from depositing high to low and low to high refractive index materials when depositing other than quarter-wavelength optical thickness layers, and to supplement the transmission data where said data indicates low sensitivity to quarter-wave optical thickness layer fabrication results.

A preferred embodiment of the recited method of monitoring and/or controlling fabrication of multiple High/Low Refractive Index Layer Band-Reject Filters further comprises a step of determining a wavelength range, around the reject band of wavelengths, in which transmisivity of the Band reject Filter being fabricated is expected to be relatively constant, and during the step e. determination of Ellipsometric Data vs. wavelength, and limiting determination of the ellipsometric Data vs. wavelength using only that range of wavelengths. Said preferred embodiment can also include excluding the central reject band wavelengths during said ellipsometric Data vs. wavelength determination.

A more detailed recitation of the disclosed invention methodology for monitoring and/or controlling fabrication of multiple High/Low Refractive Index Layer Band-Reject Filters which reject a central band of wavelengths while passing wavelengths outside thereof, comprises the steps of;

practicing steps a and b in either order:

a. providing a system for fabricating Band-Reject Filters which comprises means for depositing alternating layers of High and Low refractive Index materials onto a substrate; and b. providing a spectroscopic ellipsometer system and a source of non-ellipsometric electromagnetic wavelength(s);

practicing steps c and c' in either order:

c. applying said spectroscopic ellipsometer system to said system for fabricating Band-Reject Filters such that a substrate can be monitored in a transmission mode, by an intermediate wavelength band beam of polarized spectroscopic electromagnetic radiation provided by said spectroscopic ellipsometer system, said spectroscopic ellipsometer system being oriented so as to direct a beam of polarized spectroscopic electromagnetic radiation onto said substrate surface at an oblique angle;

c'. applying said source of non-ellipsometric electromagnetic wavelength(s) to said system for fabricating Band-Reject Filters such that a substrate can be monitored in a transmissive mode by a beam of non-ellipsometric electromagnetic radiation which is provided thereby, said beam of non-ellipsometric electromagnetic radiation being oriented so as to approach said substrate along a normal to the surface thereof;

d. placing a substrate into said system for fabricating Band reject Filters;

e. in conjunction with the other steps, determining an intermediate wavelength band range around a central reject band of wavelength of the Band-Reject Filter in which transmisivity thereof to a beam of electromagnetic radiation impinged at an oblique angle to a surface thereof is expected to be relatively constant;

f. while depositing a plurality of alternating High and Low Refractive Index layers onto said substrate, determining both non-ellipsometric transmission data, and Ellipsometric Data vs, wavelength data in the intermediate wavelength band range of wavelengths identified in step e., said determined transmission data comprising a sequence of extrema turning points in a plot of transmission intensity vs. layer number, and said determined ellipsometric DATA comprising a sequence of DATA values vs. wavelength;

g. utilizing the resulting Transmission intensity extrema turning point and Ellipsometric DATA vs. wavelength data to monitor and/or control the fabrication process, said intensity extrema turning point data being primarily used to determine when to change from depositing high to low and low to high refractive index materials when depositing quarter-wavelength optical thickness layers, and said ellipsometric DATA vs. wavelength data being primarily used to determine when to change from depositing high to low and low to high refractive index materials when depositing other than quarter-wavelength optical thickness layers, and otherwise supplementing the intensity extrema turning point data.

Similar to the methodology in the fabrication of Band-Pass Filters, said method of monitoring and controlling fabrication of Band-Reject Filters can include excluding the central reject band wavelengths from the range of wavelengths over which the ellipsometric DATA vs. wavelength is determined as identified in step e., and utilized in step f.

It is further noted that the disclosed invention can be applied to multiple layer filters which are not strictly Band Pass or Band Reject, but rather present what can be termed a Varied Attenuation vs. Wavelength characteristic. In this case as well, the disclosed invention provides for identification of an intermediate wavelength band range, or ranges, in which reflectivity and/or transmisivity thereof to a beam of electromagnetic radiation impinged at an oblique angle to a surface thereof is expected to be relatively constant, and the use of data acquired only in said intermediate wavelength band range or ranges in determining ellipsometric parameters, (ie. PSI and/or DELTA and/or combinations thereof and/or mathematical equivalents thereto).

A method of monitoring and/or controlling fabrication of multiple layer filters which present with a Varied Attenuation vs. wavelength characteristic, comprises the steps of;

a. providing a system for fabricating multiple layer filters which comprises means for depositing alternating layers of high and low refractive Index materials onto a substrate; and b. providing a spectroscopic ellipsometer system;

c. applying said spectroscopic ellipsometer system to said system for fabricating multiple layer filters such that a substrate can be monitored in a reflective and/or transmissive mode, by an intermediate wavelength band beam of polarized spectroscopic electromagnetic radiation provided by said spectroscopic ellipsometer system, said spectroscopic ellipsometer system being oriented so as to direct an intermediate wavelength band beam of polarized spectroscopic electromagnetic radiation onto said substrate surface at an oblique angle;

d. placing a substrate into said system for fabricating band-pass filters;

e. in conjunction with the other steps, determining intermediate wavelength band range(s) in which reflectivity and/or transmission to a beam of electromagnetic radiation impinged at an oblique angle to a surface thereof is/are expected to be relatively constant;

f. while depositing a plurality of alternating high and low refractive Index layers onto said substrate, determining ellipsometric PSI and/or DELTA from least one selection from the group consisting of:
  reflection data; and
  transmission data, vs. wavelength in the range(s) of intermediate band wavelengths identified in step e;

g. utilizing the resulting reflection and/or transmission ellipsometric PSI and/or DELTA vs. wavelength data to monitor and/or control the fabrication process.

Said method of monitoring and/or controlling fabrication of multiple layer filters can also involve excluding high/low reflectivity and/or transmissivity wavelength bands in wavelength regions of otherwise relatively constant low/high reflectivity and/or transmissivity, when determining ellipsometric PSI and/or DELTA.

And said method of monitoring and/or controlling fabrication of multiple layer filters can further comprise the steps of:

b'. providing a transmission monitoring system comprising a source of non-ellipsometric electromagnetic radiation and a detector; and c'. applying said transmission monitoring system such that a substrate can be monitored in a transmissive mode by a beam of electromagnetic radiation which is provided by said source of non-ellipsometric electromagnetic radiation, said transmission monitoring system being oriented to direct a beam electromagnetic radiation substantially along a normal to the surface of the substrate; and using non-ellipsometric transmission data obtained at a substantially normal angle of incidence, which data comprises a sequence of extrema turning points in a plot of transmission intensity vs. layer number, and using said extrema turning points to determine when to change from depositing high to low and low to high refractive index materials when depositing quarter-wavelength optical thickness layers. Said method can include using determined ellipsometric PSI and/or DELTA data aid with that determination, and to determine when to change from depositing high to low and low to high refractive index materials when depositing other than quarter-wavelength optical thickness layers.

It is disclosed that, while not limiting, a preferred spectroscopic ellipsometer system for application in practicing the disclosed invention is a rotating compensator sample system investigation system comprising a source of a polychromatic beam of electromagnetic radiation, a polarizer, a stage for supporting a sample system, an analyzer, a dispersive optics and at least one detector system which contains a multiplicity of detector elements. In addition, said spectroscopic rotating compensator sample system investigation system further comprises at least one compensator(s) positioned at a location selected from the group consisting of: (before said stage for supporting a sample system, and after said stage for supporting a sample system, and both before and after said stage for supporting a sample system). When said spectroscopic rotating compensator sample system investigation system is used to investigate a sample system present on said stage for supporting a sample system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said sample system, (ie. a multiple layer high/low refractive index material filter being fabricated), pass through said analyzer and interact with said dispersive optics such that a multiplicity of essentially single wavelengths are caused to simultaneously enter a corresponding multiplicity of detector elements in said at least one detector system. The described rotating compensator ellipsometer system is sold by the J.A. Woollam CO. under the Trademark M2000, and is protected by U.S. Pat. No. 5,872,630.

The disclosed invention will be better understood by reference to the Detailed Description Section of this Specification, in combination with the Drawings.

SUMMARY OF THE INVENTION

It is therefore a primary purpose and/or objective of the disclosed invention to teach a method of manufacturing multilayer, thin film band pass, band reject and/or varied attenuation interference filters, comprising the steps of:
  depositing a plurality of thin film layers on a substrate, the plurality of thin film layers forming a multilayer, thin film interference filter;
  monitoring the formation of at least some of the thin film layers during the deposition process, said monitoring step including the steps of:
    directing an intermediate band radiation probe to reflect off the layers on the substrate;
    monitoring the change in polarization state of the probe beam induced by the interaction with the layers and generating output signals in response thereto; and
    controlling the deposition process based on the monitored signal.

It is another purpose and/or objective of the disclosed invention to teach a method which is useful in the fabrication of multiple layer high/low refractive index filter structures, which method utilizes spectroscopic ellipsometry in an intermediate band of wavelengths, where "intermediate" is defined as a band of wavelengths around a pass or reject band, in which the reflectivity or transmisivity is relatively constant.

In conjunction with other purposes and/or objectives, it is further a purpose and/or objective of the disclosed invention to teach:
  use of ellipsometric PSI and/or DELTA vs. Wavelength data determined at an oblique angle of incidence over an intermediate band wavelength range, or ranges in which the reflectivity or transmisivity is relatively constant, from which intermediate band wavelength range or ranges certain wavelength(s) are optionally excluded, in monitoring and/or controlling the fabrication of multiple layer high/low refractive index, filter structures.

It is a further purpose and/or objective of the disclosed invention to teach combined use of:
  ellipsometric PSI and/or DELTA vs. Wavelength data determined at an oblique angle of incidence over an intermediate wavelength band range in which wavelength range the reflectivity or transmisivity is relatively constant, from which wavelength range certain pass or reject band per se. wavelength(s) are optionally excluded, and
  transmission intensity extrema turning point data;

in monitoring and/or controlling the fabrication of multiple layer, high/low refractive index, filter structures.

Other objectives and/or purposes will become apparent from a reading of the Specification and Claims.

DETAILED DESCRIPTION

Figure 1:
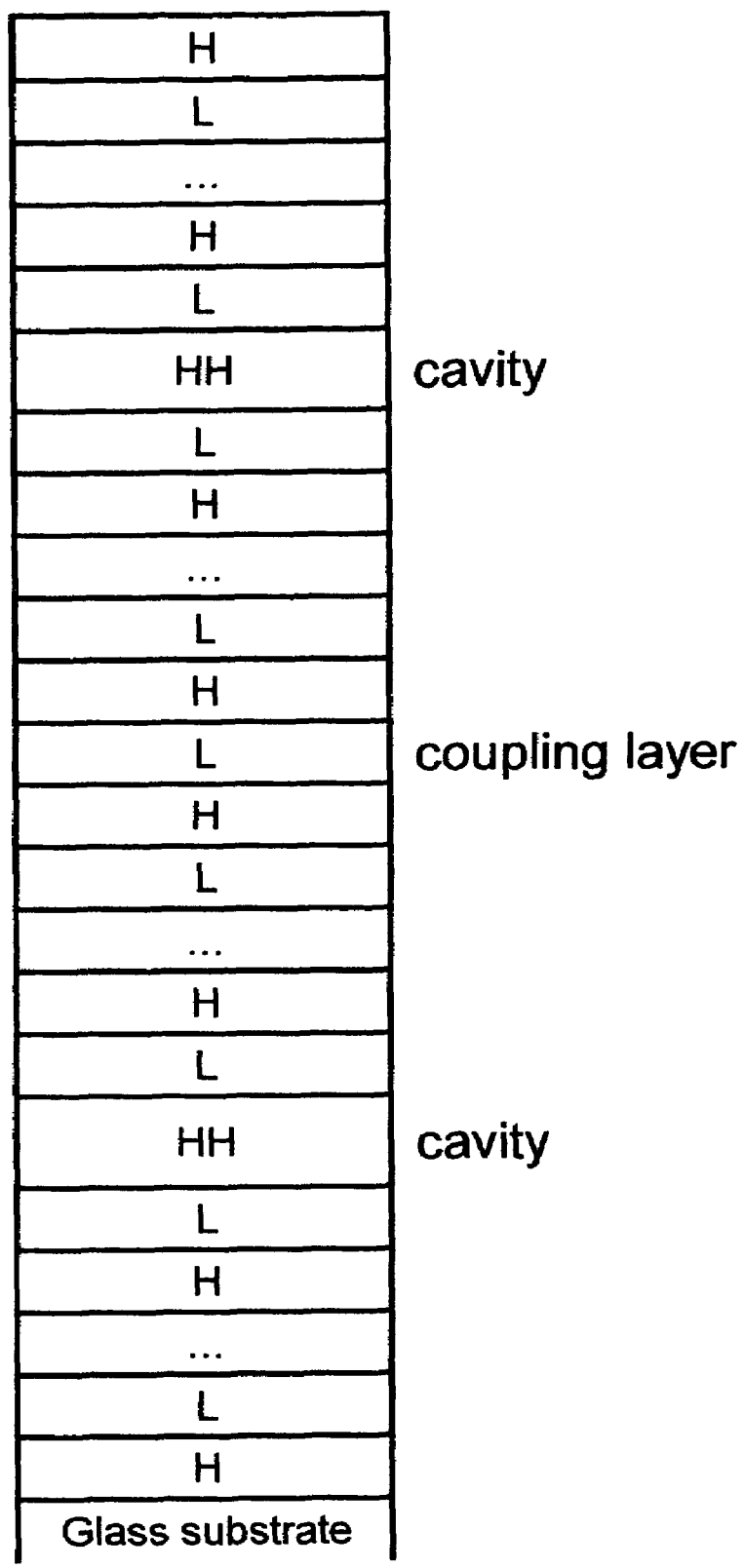
FIG. 1, shows a schematic of a 2-cavity dielectric narrow Band-Pass optical filter structure.

Turning now to FIG. 1, it should be appreciated that a schematic of a demonstrative 2-cavity all dielectric narrow Band-Pass optical filter structure is shown.

Figure 3:
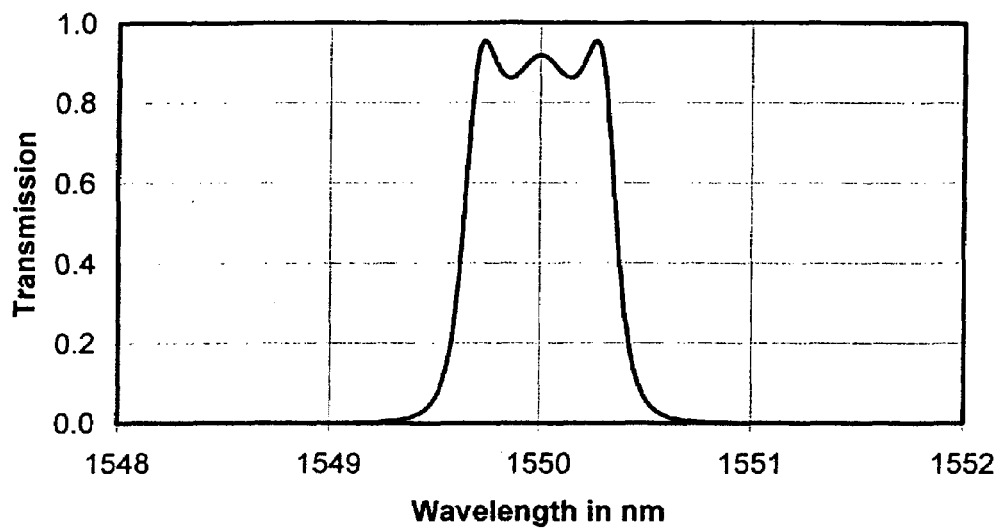
FIG. 3 shows a typical Transmission characteristic for the 3-cavity narrow Band-Pass optical filter over a wavelength range of 1548 to 1552 nm.
Figure 2:
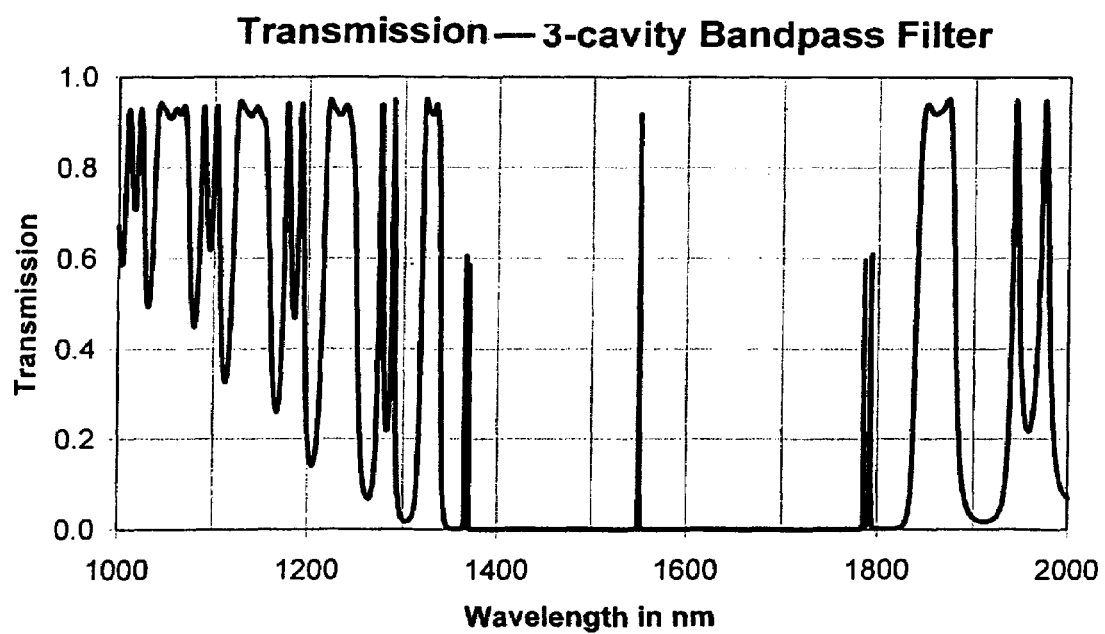
FIG. 2 shows the Transmission characteristic for a 3-cavity narrow Band-Pass optical filter fabricated similar to the demonstrative two-cavity system shown in FIG. 1, over a range of 1000 to 2000 nm.

FIG. 2 shows the Transmission characteristic for a 3-cavity narrow Band-Pass optical filter (fabricated similar to the 2-cavity system shown in FIG. 1), over a broad range of 1000 to 2000 nm. FIG. 3 shows the Transmission characteristic for the 3-cavity narrow Band-Pass optical filter over an intermediate wavelength range of 1548 to 1552 nm.

(Note that FIGS. 2 and 3 can be considered demonstrative of fabricatable stacked layer Band-Reject Filter characteristics as well, if the "Y" axis is labeled Reflection or Rejection instead of Transmission, and it is to be understood that the disclosed invention is similarly applicable to fabrication monitor/control of both Band-Pass and Band-Reject as well as to Varied Attenuation vs. Wavelength stacked layer Filters. The major distinction being that Reflection ellipsometry is applicable where Band-Pass stacked layer Filters are fabricated, whereas Transmission ellipsometry is primarily applicable where Band-Reject stacked layer Filters are fabricated, and where either, or both, reflection and transmission ellipsometry can be applied where Varied Attenuation vs. Wavelength stacked layer Filters are fabricated).

Figure 4:
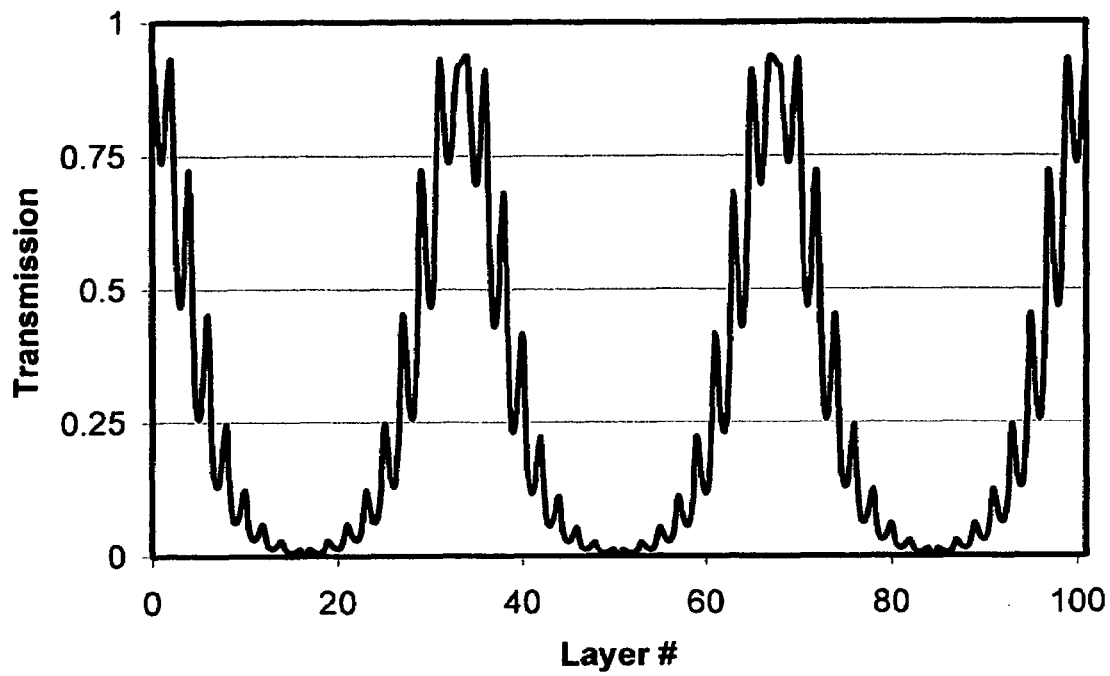
FIG. 4 demonstrates a typical "extrema" featuring plot of electromagnetic beam intensity Transmission vs. Number of Layers, (eg. between 0 and 100).
Figure 5:
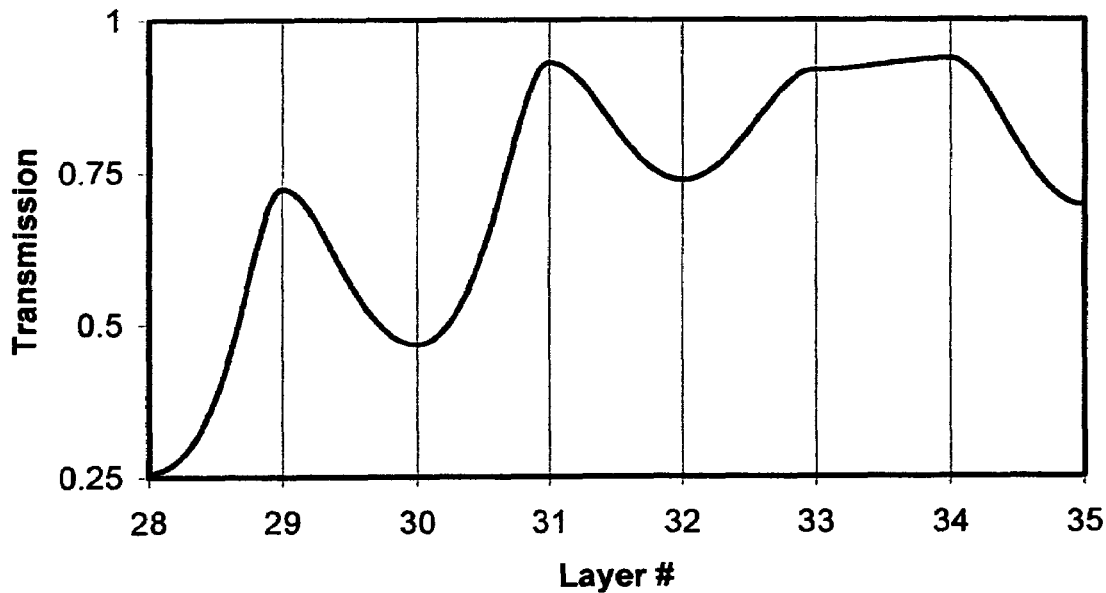
FIG. 5 show a region of FIG. 4 in which the region involving Layers 28 to 35 is expanded.

FIG. 4 demonstrates a typical "extrema" featuring plot of electromagnetic beam Intensity Transmission vs. Number of Layers, (eg. between 0 and 100), and FIG. 5 show a region of FIG. 4 in which the region involving Layers 28 to 35 is expanded. The important thing to note is that the Transmission plot in FIG. 5 shows low sensitivity at layers 33 to 34. The point demonstrated is that use of Transmission data as shown, enables less than optimum monitoring and/or control during fabrication of some layers of a multi-layer narrow Band-Pass optical filter. This is an on-going fabrication control problem faced by industry.

Figure 6:
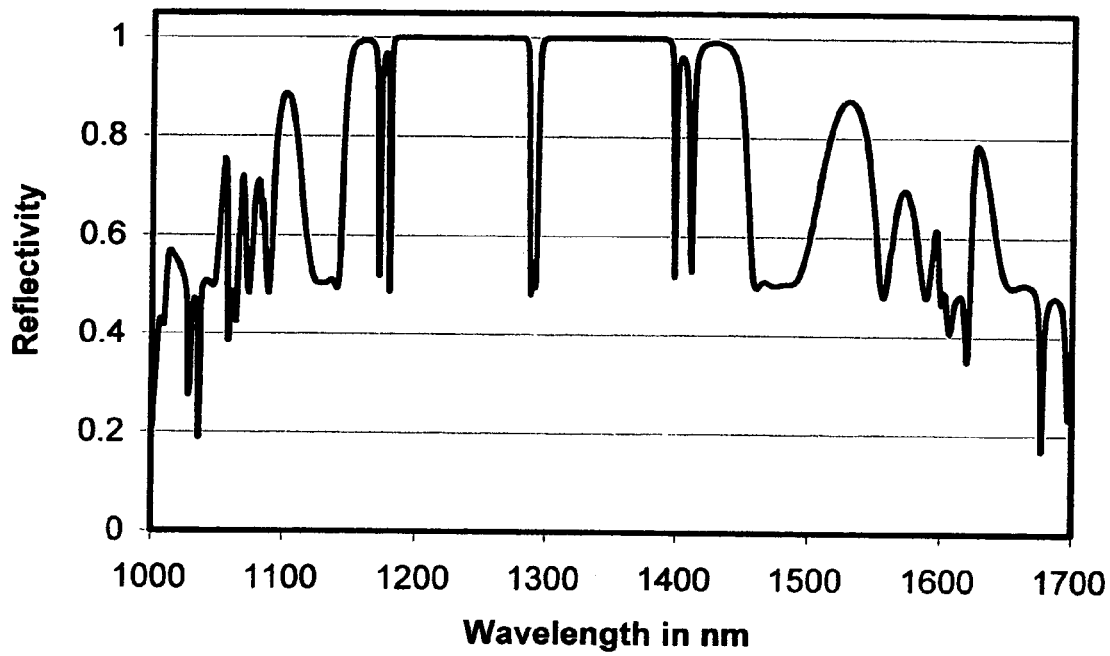
FIG. 6 shows a Reflectivity plot over a broad range of wavelengths from 1000 to 1700 nm. Note the intermediate wavelength band range of 1180 to 1380 nm, which wavelength range corresponds to the range of essentially 100% reflectivity.
Figure 7:
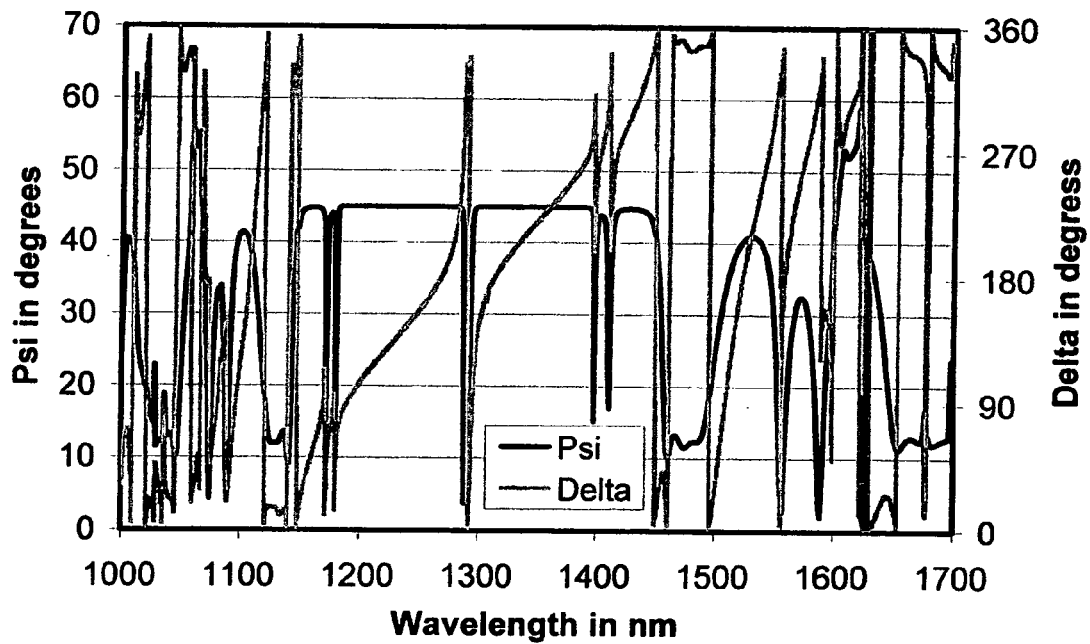
FIG. 7 shows ellipsometric PSI and DELTA vs. wavelength determine cover the same wavelength range as represented in FIG. 6. Again, note the intermediate wavelength band range of 1180 to 1380 nm, which wavelength range corresponds to the range of essentially 100% reflectivity.
Figure 8:
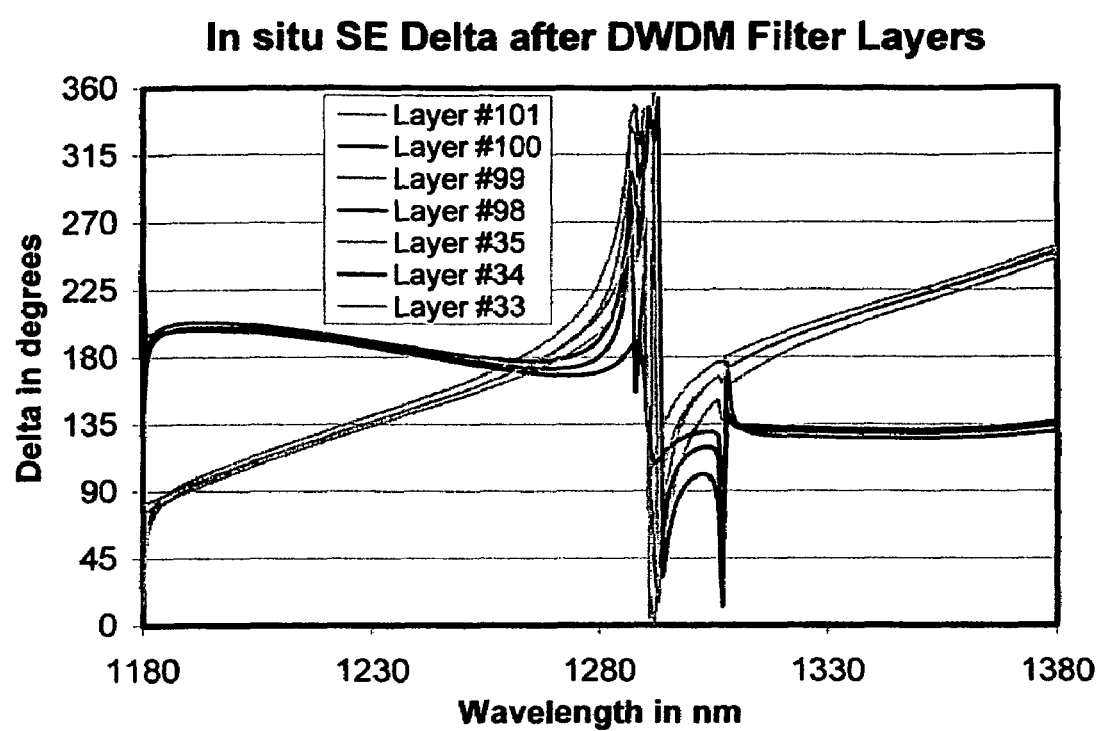
FIG. 8 shows ellipsometric DELTA over the intermediate wavelength band range of 1180 to 1380 nm, which wavelength range corresponds to the range of essentially 100% reflectivity identified in FIG. 6.

Turning now to FIGS. 6, 7 and 8, there is shown data for a narrow passband optical filter, which passband is centered around 1280 nm when electromagnetic radiation is impinged thereupon at an oblique angle of seventy (70) degrees from a normal to the narrow Band-Pass optical filter surface. Note that a narrow passband optical filter with a passband at 1550 nm, (as shown in FIGS. 3 and 4), determined using an electromagnetic beam entered along a normal to the surface of the narrow passband optical filter, is typically shifted to a passband centered at other than 1550 nm, (eg. 1280 nm), such indicated in FIGS. 6, 7 and 8, when a beam of electromagnetic radiation is entered at an oblique angle, (eg. 70 degrees) from a normal to said surface.

FIG. 6 shows a Reflectivity plot over a broad range of wavelengths from 1000 to 1700 nm. FIG. 7 shows ellipsometric PSI and DELTA determine cover the same wavelength range as represented in FIG. 6. FIG. 8 shows ellipsometric DELTA over the intermediate band range of wavelengths 1180 to 1380, which intermediate wavelength range is defined by and corresponds to the range of essentially 100% reflectivity identified in FIG. 6. Note that two very distinct and easily differentiated groupings of DELTA values are present, over the range of wavelengths shown in FIG. 8. One of said DELTA groupings corresponds to high refractive index material, and the other thereof corresponds to low refractive index material. In that the ellipsometric DELTA is related to a thin film optical thickness, (ie. the refractive index multiplied by the physical thickness), the benefit of the present approach to monitoring quarter wavelength layers in High/Low narrow bandwidth optical filters can be appreciated. And, as mentioned, said ellipsometric DELTA data being determined in an intermediate band wavelength range where reflectivity is essentially 100%, provides information relevant to the surface layer, and said data is not significantly affected by previously deposited layers.

The disclosed invention method then, with respect to fabricating Band Pass Filters, focuses on determination of ellipsometric DELTA over an determined intermediate range of wavelengths which is centered around a central passband wavelength in a multiple layer High/Low stack narrow passband optical filter, over which determined intermediate band range of wavelengths the oblique angle of incidence reflectivity of the multiple layer High/Low stack narrow passband optical filter, is essentially 100%. The preferred embodiment of the disclosed invention method does not utilize wavelengths outside said determined intermediate range of wavelengths when determining ellipsometric DELTA, and optionally also deletes passband wavelengths. Determination of the appropriate intermediate wavelength band range of wavelengths can be performed in a completely separate Reflectivity monitoring step, or can be determined from collected ellipsometric data essentially simultaneous with use thereof in determining ellipsometric DELTA by, for instance, a mathematical regression of acquired data onto a proposed mathematical model.

It is noted also that reflection ellipsometric PSI is typically more dependent on non-idealities, such as surface roughness and refractive index grading in a thin layer, than it is to optical thickness as is ellipsometric DELTA, hence it is not typically utilized in fabricating Band Pass Multiple Layer Filters and the preferred approach under relevant disclosed invention teachings, is to discard the ellipsometric PSI data.

A variation of the disclosed invention method combines:
   conventional determination of transmission turning points, (see FIG. 4 demonstration thereof), via use of normal incidence electromagnetic radiation set at the passband wavelength, and
   determination of ellipsometric DELTA vs. wavelength over an intermediate band range of wavelengths around said passband wavelength wherein reflectivity is essentially 100%, via use of spectroscopic oblique incidence electromagnetic radiation around the narrow passband wavelength.

Said combined approach enables better control, via use of ellipsometric DELTA vs. wavelength data obtained at oblique angle, over non-quarter wavelength thick cavity growth, and said ellipsometric DELTA vs. wavelength data can supplement transmission turning point data in regions wherein sensitivity is low, (eg. see low slope Transmission plot in FIG. 5 at layers 33 to 34).

Figure 9:
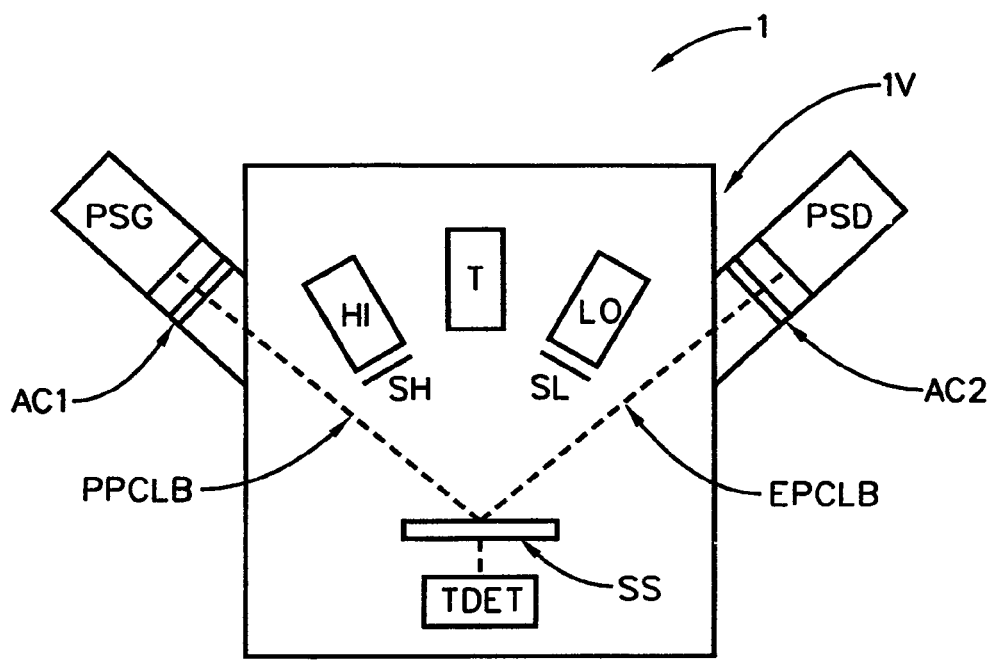
FIG. 9 demonstrates a deposition system generally representative of that in which Band-Pass filter structures can be fabricated.
Figure 10:
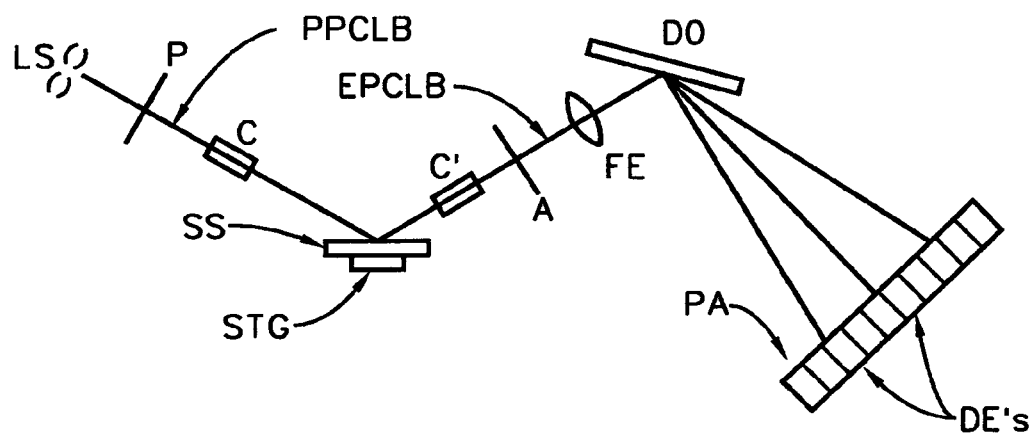
FIG. 10 demonstrates a Rotating Compensator Ellipsometer System, as Claimed in U.S. Pat. No. 5,872,630 configured in a reflection mode.

To provide general insight to systems for practicing the disclosed invention, FIGS. 9 and 10 are included. FIG. 9 demonstrates a deposition system (1) comprising a Vacuum Chamber (1V), (which during use is held at low internal pressure, eg. $10^{-9}$ Tor), to Vacuum Chamber (1V) is affixed Polarization Stage Generator (PSG) and Polarization State Detector (PSD) Systems. The Polarization State Generator (PSG) provides an electromagnetic beam, (oblique angled dashed line (PPCLB)), which reflects from the surface of a Sample System (SS) and enters the Polarization State Detector (PSD), (oblique angled dashed line (EPCLB)). The (PSG) and (PSD) are external to the Vacuum Chamber (1V) in ambient atmosphere, and that Windows (AC1) and (AC2) provide pressure difference interfacing. (Note that U.S. Pat. No. 6,034,777 describes how to compensate for the effects of said Windows when determining ellipsometric DELTA's, and that said 777 patent is incorporated herein by reference).

Also shown is a Transmission Source (T) of a beam of electromagnetic radiation, (vertical dashed line), and a Transmission Detector (TDET) for use in Transmission investigation of the Sample System (SS). Also shown are means for depositing high (HI) and low (LO) refractive index materials, with shutters (SH) and (SL), respectively providing controlled access of materials provided therefrom to the Sample System (SS). The Transmission Source (T) and Detector (TDET) are shown present in the Vacuum Chamber (1V), but it is to be understood that they can be external thereto, similar to the Ellipsometer components (PSG) and (PSD), just as could, the spectroscopic ellipsometer (PSG) and (PSD) be located within the Vacuum Chamber (1V). Any functional location and orientation of the ellipsometer and transmission system elements is within the scope of the disclosed invention.

While any type of ellipsometer system can be applied in practice of the disclosed invention, FIG. 10 demonstrates a Rotating Compensator Ellipsometer System, as Claimed in U.S. Pat. No. 5,872,630, (note, said 630 patent also teaches regression calibration of the Rotating Compensator Ellipsometer and said 630 patent is incorporated herein by reference). The FIG. 10 Rotating Compensator Ellipsometer System is configured in a reflection mode, (applicable to fabrication of Band-Pass stacked layer Filters), and is shown to comprise a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's). Said spectroscopic rotating compensator sample system investigation system further comprises at least one compensator(s) (C) (C') (C") positioned at a location selected from the group consisting of: (before said stage (S*TG) for supporting a sample system (SS), and after said stage (STG) for supporting a sample system (SS), and both before and after said stage (STG) for supporting a sample system (SS)). When said spectroscopic rotating compensator ellipsometer system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while a polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), and said polychromatic beam of electromagnetic radiation is also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET). Note that an optional Focusing Lens (FE) is also indicated as optionally present, and when present serves to provide a better defined spot of electromagnetic radiation tot he Dispersive Optics (DO).

To coordinate FIGS. 9 and 10, it is noted that the FIG. 9 Polarization State Generator (PSG) can be considered to be a combination of the FIG. 10 Source of Electromagnetic Radiation (LS), Polarizer (P), and perhaps Compensator (C), while the FIG. 9 Polarization State Detector (PSD) can be considered to be comprised of a combination of FIG. 10 Analyzer (A), Dispersive Optics (DO), and Detector (PA), in optional combination with the Focusing Lens (FE) and Compensator (C').

Figure 11:
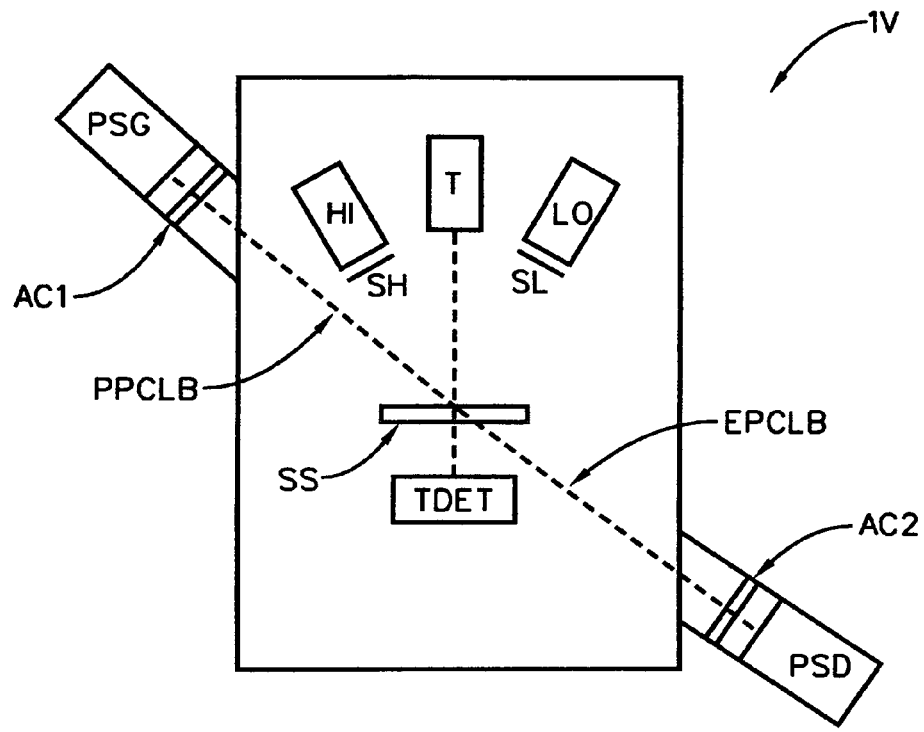
FIG. 11 demonstrates a deposition system generally representative of that in which Band-Reject filter structures can be fabricated.
Figure 12:
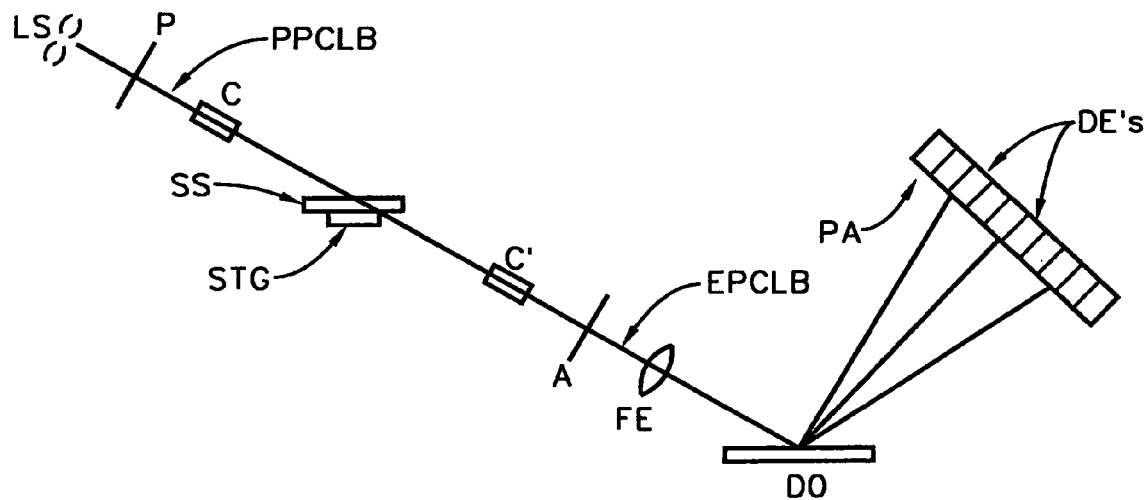
FIG. 12 demonstrates a Rotating Compensator Ellipsometer System, as Claimed in U.S. Pat. No. 5,872,630 configured in a transmission mode.

FIGS. 11 and 12 show systems similar to those in FIGS. 9 and 10, (which FIGS. 9 and 10 systems are configured to acquire reflection ellipsometric data as utilized in fabrication of Band-Pass Filters), except that the configuration shown in FIGS. 11 and 12 is appropriate for obtaining transmission ellipsometric data, as is applicable in fabrication of Band-Reject Filters.

In the foregoing, the terminology "optical thickness" should be understood to refer to the product of the refractive index and physical thickness, (n×t), of a layer of material.

While not limiting, it is noted that high and low refractive index materials from which a multiple layer, narrow pass-band optical filter can be constructed, are $Ta_2O_5$ and $SiO_2$, respectively.

It is also specifically stated that while data obtained from a Stacked Layer Narrow Band-Pass filter was used as a specific demonstrative example in disclosing the invention, as described in the Disclosure of the Invention Section of this Specification, said disclosed invention methodology is, in appropriately modified form, equally applicable to fabrication of Band Reject Stacked Layer Filters and to Varied Attenuation Stacked Layer Filters, as well as Band-Pass Multiple Layer Filters.

It is also noted that while ellipsometric PSI and DELTA are used as examples in the foregoing, functional equivalents thereto, such as Tan(PSI) or Cos(DELTA) etc. and parameters which include both PSI and DELTA, (eg. ) or equivalents thereto are to be considered as within the scope of the utilized demonstrative PSI and DELTA terminology where consistent with the context of their usage. That is, where PSI and/or DELTA is/are recited in the Claims, said usage is to be interpreted sufficiently broadly, where it makes mathematical sense to do so, to include combinations thereof and/or mathematical equivalents thereto.

Patentability is thought to be found in the application of Reflection and/or Transmission Ellipsometric Parameter(s) vs. Wavelength data in the monitoring and/or controlling of the fabrication of stacked High/Low Refractive Index layered Filters, either alone or in combination with use of Transmission Intensity Turning Point vs. Layer Number data. This is particularly thought to be the case where the wavelengths utilized in determining the ellipsometric Parameter(s) vs. Wavelength data are limited to an intermediate band range of wavelengths around a pass or reject band of wavelengths in which reflectivity or transmisivity, (eg. for Band-Pass and Band-Reject filters respectively), is relatively constant. This belief is further enhanced where data pertaining to pass band or reject band wavelengths is eliminated when determining ellipsometric Parameter(s) vs. Wavelength. Where Varied Attenuation vs. Wavelength Filters are fabricated, the disclosed invention can include use of Ellipsometric PSI and/or DELTA, (including mathematical equivalents thereof) arrived at by use of Ellipsometric Data achieved in both Reflection and Transmission, in intermediate wavelength band range(s).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of manufacturing multilayer, thin film interference filters, comprising the steps of:

depositing a plurality of thin film layers on a substrate, the plurality of thin film layers forming a multilayer, thin film interference filter;

monitoring the formation of at least some of the thin film layers during the deposition process, said monitoring step including the steps of:

directing an intermediate band radiation probe to reflect off the layers on the substrate;

monitoring the change in polarization state of the probe beam induced by the interaction with the layers and generating output signals in response thereto; and controlling the deposition process based on the monitored signal.

2. A method as in claim 1, in which the thin film interference intermediate filter is a band-pass filter, and in which intermediate band of wavelengths is defined by a region around a central pass band in which the reflectivity properties are substantially uniform.

3. A method as in claim 1, in which the thin film interference intermediate filter is a band-reject filter, and in which intermediate band of wavelengths is defined by a region around a central pass band in which the transmisivity properties are substantially uniform.

4. A method as in claim 1, in which the thin film interference intermediate filter is a varied attenuation filter, and in which intermediate band of wavelengths is defined by a region around a central pass or rejection band in which the reflectivity or transmisivity properties, respectively, are substantially uniform.

5. A method of manufacturing multilayer, thin film interference filters, comprising the steps of:

depositing a plurality of thin film layers on a substrate, the plurality of thin film layers forming a multilayer, thin film interference filter;

monitoring the formation of at least some of the thin film layers during the deposition process, said monitoring step including the steps of:

directing an intermediate band radiation probe to reflect off the layers on the substrate;

monitoring the change in polarization state of the probe beam induced by the interaction with the layers and generating output signals in response thereto; and controlling the deposition process based on the monitored signal;

said thin film interference intermediate filter being a band-pass filter, and in which intermediate band of wavelengths is defined by a region around a central pass band in which the reflectivity properties are substantially uniform.

6. A method of manufacturing multilayer, thin film interference filters, comprising the steps of:

depositing a plurality of thin film layers on a substrate, the plurality of thin film layers forming a multilayer, thin film interference filter;

monitoring the formation of at least some of the thin film layers during the deposition process, said monitoring step including the steps of:

directing an intermediate band radiation probe to reflect off the layers on the substrate;

monitoring the change in polarization state of the probe beam induced by the interaction with the layers and generating output signals in response thereto; and controlling the deposition process based on the monitored signal;

said thin film interference intermediate filter being a band-reject filter, and in which intermediate band of wavelengths is defined by a region around a central pass band in which the transmisivity properties are substantially uniform.

7. A method as in claim 1, in which the steps of:

directing an intermediate band radiation probe to reflect off the layers on the substrate; and monitoring the change in polarization state of the probe beam induced by the interaction with the layers and generating output signals in response thereto;

involves utilizing a spectroscopic rotating compensator sample system (SS) investigation system comprising a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's), said spectroscopic rotating compensator sample system investigation system further comprising at least one compensator(s) (C) (C') (C") positioned at a location selected from the group consisting of: (before said stage (STG) for supporting a sample system (SS), and after said stage (STG) for supporting a sample system (SS), and both before and after said stage (STG) for supporting a sample system (SS)); such that when said spectroscopic rotating compensator sample system investigation system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while an intermediate wavelength band polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), said intermediate wavelength band polychromatic beam of electromagnetic radiation being also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET).

8. A method as in claim 2, in which the steps of:

directing an intermediate band radiation probe to reflect off the layers on the substrate; and monitoring the change in polarization state of the probe beam induced by the interaction with the layers and generating output signals in response thereto;

involves utilizing a spectroscopic rotating compensator sample system (SS) investigation system comprising a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's), said spectroscopic rotating compensator sample system investigation system further comprising at least one compensator(s) (C) (C') (C") positioned at a location selected from the group consisting of:

before said stage (STG) for supporting a sample system (SS);

after said stage (STG) for supporting a sample system (SS); and both before and after said stage (STG) for supporting a sample system (SS);

such that when said spectroscopic rotating compensator sample system investigation system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while an intermediate wavelength band polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), said intermediate wavelength band polychromatic beam of electromagnetic radiation being also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET).

9. A method as in claim 3, in which the steps of:
directing an intermediate band radiation probe to reflect off the layers on the substrate; and
monitoring the change in polarization state of the probe beam induced by the interaction with the layers and generating output signals in response thereto;
involves utilizing a spectroscopic rotating compensator sample system (SS) investigation system comprising a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's), said spectroscopic rotating compensator sample system investigation system further comprising at least one compensator (s) (C) (C') (C") positioned at a location selected from the group consisting of:
before said stage (STG) for supporting a sample system (SS);
after said stage (STG) for supporting a sample system (SS); and
both before and after said stage (STG) for supporting a sample system (SS);
such that when said spectroscopic rotating compensator sample system investigation system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while an intermediate wavelength band polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), said intermediate wavelength band polychromatic beam of electromagnetic radiation being also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET).

10. A method as in claim 4, in which the steps of:
directing an intermediate band radiation probe to reflect off the layers on the substrate; and
monitoring the change in polarization state of the probe beam induced by the interaction with the layers and generating output signals in response thereto;
involves utilizing a spectroscopic rotating compensator sample system (SS) investigation system comprising a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's), said spectroscopic rotating compensator sample system investigation system further comprising at least one compensator (s) (C) (C') (C") positioned at a location selected from the group consisting of:
before said stage (STG) for supporting a sample system (SS);
after said stage (STG) for supporting a sample system (SS); and
both before and after said stage (STG) for supporting a sample system (SS);
such that when said spectroscopic rotating compensator sample system investigation system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while an intermediate wavelength band polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), said intermediate wavelength band polychromatic beam of electromagnetic radiation being also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET).

11. A method as in claim 5, in which the steps of:
directing an intermediate band radiation probe to reflect off the layers on the substrate; and
monitoring the change in polarization state of the probe beam induced by the interaction with the layers and generating output signals in response thereto;
involves utilizing a spectroscopic rotating compensator sample system (SS) investigation system comprising a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's), said spectroscopic rotating compensator sample system investigation system further comprising at least one compensator (s) (C) (C') (C") positioned at a location selected from the group consisting of:
before said stage (STG) for supporting a sample system (SS);
after said stage (STG) for supporting a sample system (SS); and
both before and after said stage (STG) for supporting a sample system (SS);
such that when said spectroscopic rotating compensator sample system investigation system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while an intermediate wavelength band polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), said intermediate wavelength band polychromatic beam of electromagnetic radiation being also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET).

12. A method as in claim 6, in which the steps of:
    directing an intermediate band radiation probe to reflect off the layers on the substrate; and
    monitoring the change in polarization state of the probe beam induced by the interaction with the layers and generating output signals in response thereto;
involves utilizing a spectroscopic rotating compensator sample system (SS) investigation system comprising a source (LS) of a polychromatic beam of electromagnetic radiation (PPCLB), a polarizer (P), a stage (STG) for supporting a sample system, an analyzer (A), a dispersive optics (DO) and at least one detector system (DET) which contains a multiplicity of detector elements (DE's), said spectroscopic rotating compensator sample system investigation system further comprising at least one compensator (s) (C) (C') (C") positioned at a location selected from the group consisting of:
    before said stage (STG) for supporting a sample system (SS);
    after said stage (STG) for supporting a sample system (SS); and
    both before and after said stage (STG) for supporting a sample system (SS);
such that when said spectroscopic rotating compensator sample system investigation system is used to investigate a sample system (SS) present on said stage (STG) for supporting a sample system, said analyzer (A) and polarizer (P) are maintained essentially fixed in position and at least one of said at least one compensator(s) (C) (C') (C") is caused to continuously rotate while an intermediate wavelength band polychromatic beam of electromagnetic radiation (PPCLB) produced by said source (LS) of a polychromatic beam of electromagnetic radiation (PPCLB) is caused to pass through said polarizer (P) and said compensator(s) (C) (C') (C"), said intermediate wavelength band polychromatic beam of electromagnetic radiation being also caused to interact with said sample system (SS), pass through said analyzer (A) and interact with said dispersive optics (DO) such that a multiplicity of essentially single wavelengths are caused to simultaneously enter a corresponding multiplicity of detector elements (DE's) in said at least one detector system (DET).

13. A method as in claim 2 in which the wavelengths in the pass band are not monitored for change in polarization state during deposition.

14. A method as in claim 3 in which the wavelengths in the reject band are not monitored for change in polarization state during deposition.

15. A method as in claim 5 in which the wavelengths in the pass band are not monitored for change in polarization state during deposition.

16. A method as in claim 6 in which the wavelengths in the reject band are not monitored for change in polarization state during deposition.

17. A method as in claim 4 in which the wavelengths in the pass or reject band are not monitored for change in polarization state during deposition.

* * * * *

UNITED STATES PATENT AND TRADEMARK OFFICE
CERTIFICATE OF CORRECTION

PATENT NO. : 7,295,313 B1  
APPLICATION NO. : 10/943821  
DATED : November 13, 2007  
INVENTOR(S) : Johs et al.

Page 1 of 1

It is certified that error appears in the above-identified patent and that said Letters Patent is hereby corrected as shown below:

Title page, item (73) Assignee: Delete "Wollam" and insert --Woollam--.

Signed and Sealed this

Fifteenth Day of April, 2008

JON W. DUDAS  
*Director of the United States Patent and Trademark Office*